United States Patent [19]

Cometti et al.

[11] Patent Number: 5,344,960
[45] Date of Patent: Sep. 6, 1994

[54] CATALYST FOR CARBONYLATING NAPHTHALENE MONO- AND DISULFONATES AND PROCESS USING SAID CATALYST

[75] Inventors: Giuseppe Cometti, Verbania-Pallanza; Annick Du Vosel, Caltignaga; Franco Francalanci; Roberto Santi, both of Novara, all of Italy

[73] Assignee: Enichem S.p.A., Milan, Italy

[21] Appl. No.: 163,114

[22] Filed: Dec. 6, 1993

[30] Foreign Application Priority Data

Dec. 11, 1992 [IT] Italy ...................... MI 92 A/002818

[51] Int. Cl.$^5$ .......................... C07C 69/76; B01J 31/00
[52] U.S. Cl. ................................. 560/100; 562/406; 502/151; 502/155
[58] Field of Search ....................... 560/100; 562/406; 502/151, 155

[56] References Cited

U.S. PATENT DOCUMENTS

| | | | |
|---|---|---|---|
| 4,506,092 | 3/1985 | Lentz et al. | 560/100 |
| 4,594,445 | 6/1986 | Lentz et al. | 560/100 |
| 5,095,135 | 3/1992 | Yamada et al. | 560/100 |

FOREIGN PATENT DOCUMENTS 146291 6/1985 .

*Primary Examiner*—Paul J. Killos
*Attorney, Agent, or Firm*—George P. Hoare, Jr.

[57] ABSTRACT

A cobalt based catalyst, and the method for preparing it, are disclosed. The catalyst is obtained from the reaction between $NaCo(CO)_4$ and s-trichloro triazine and is advantageously used in the processes of carbonylation of naphthalene mono- and disulfonates in order to yield naphthalene esters and acids.

14 Claims, No Drawings

CATALYST FOR CARBONYLATING NAPHTHALENE MONO- AND DISULFONATES AND PROCESS USING SAID CATALYST

The present invention relates to a cobalt-based catalyst for carbonylating naphthalene mono- and disulfonates by means of carbon monoxide, in an alcoholic solvent.

Furthermore, the invention relates to the method for preparing such a catalyst, and to a process in which the novel catalyst is used, in order to produce naphthalene esters and acids.

The catalyst is obtained by causing $NaCo(CO)_4$ to react with s-trichloro triazine, a component, the latter, which results to be cheaper than those used according to the prior art, and which is capable of conferring a higher heat stability to the catalyst.

In Italian patent No. 1,205,284 a catalyst for the carbonylation of aromatic halides and aromatic sulfonates is disclosed, which is obtained by means of the reaction between the sodium salt of cobalt tetracarbonyL $NaCo(CO)_4$ and a co-catalyst. Such a catalyst, in its active form, is represented by the following formula:

$$Y-Co(CO)_4 \qquad (I)$$

in which Y is a group selected from $-CH_2-COOR$, wherein R is an alkyl group of up to 8 carbon atoms; a perfluoro alkyl group of up to 8 carbon atoms; a $-CH_2CN$ group; an alkyl group of up to 8 carbon atoms.

The strong points of this catalytic system are the possibility of operating under mild temperature and pressure conditions and during short reaction times; on the other hand, the heat instability of the catalyst and the high costs for the co-catalyst (dimethyl sulphate or ethyl bromoacetate) cause problems of operating type such as, e.g., the need for heating the pre-formed catalyst at low temperature (from $-10°$ C. to $0°$ C.) and of process cheapness.

Therefore, the need existed for finding new catalysts with more suitable characteristics for being used in a facility of industrial type.

The present Applicant has found now, and it is a first object of the present inventiont an improved catalyst for naphthalene mono- and disulfonates carbonylation having the formula (II):

$$Z-Co(CO)_4 \qquad (II)$$

in which Z stands for the 2,5-dichloro-1,3,5-triazinyl radical:

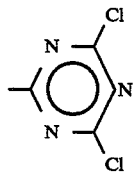

The present invention relates as well to the method for preparing such a catalyst, which method consists in causing the sodium salt of cobalt tetracarbonyl NaCo(CO)$_4$ to react with s-trichtoro triazine, in an ether solvent, at temperatures comprised within the range of from $-10°$ C. to $25°$ C., subsequently submitting the solution to filtration in order to remove any precipitated sodium chloride.

A last object of the present invention is constituted by a process for preparing naphthalene esters and acids which consists in carbonylating naphthalene mono- and disulfonates with carbon monoxide, an alcoholic solvent, under atmospheric pressure, at temperatures comprised within the range of from $-20°$ C. to $60°$ C., in the presence of an acidity acceptor compound and of a catalyst which, in its active form, is constituted by a cobalt complex of formula (II).

The catalysts according to the present invention display several advantages over the catalysts used heretofore:
- they requi re lower costs and are obtained from commercially available products;
- they are more stable, therefore make it possible the carbonylation reaction to be carried out at room temperature and at atmospheric pressure;
- they are less toxic;
- they are easily prepared.

The formation of the catalyst of formula (II) is surprising, because s-trichloro triazine is a chloro derivative of the heteroaromatic series and, according to the known art, it should not interact with the cobalt salt $NaCo(CO)_4$.

The catalyst of formula (II), according to the present invention, is prepared, as already mentioned, by causing $NaCo(CO)_4$ to react with s-trichloro triazine according to the reaction:

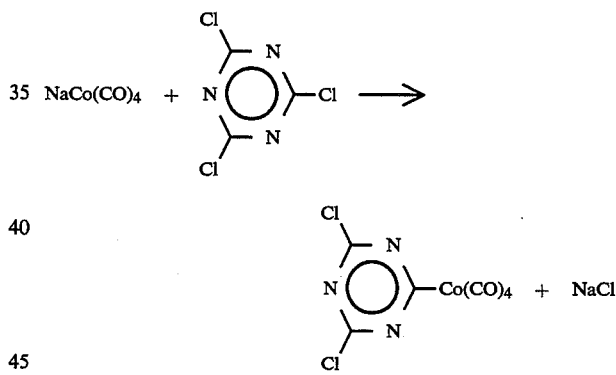

The reactants are normally available from the market.

The reaction is carried out in the presence of an organic solvent; preferably, ether is used.

The reaction temperature generally is comprised within the range of from $0°$ C. to $25°$ C., with $0°$ C. being the preferred temperature.

The reaction is complete within a reaction time comprised within the range of from 1 to 3 hours.

During the reaction, sodium chloride which is formed, precipitates, and is filtered off at reaction end, after increasing the reaction mixture temperature up to $25°$ C.

The I.R. analysis of the ethereal solution, after filtration, displays the disappearance of the absorption band at 1900 cm$^{-1}$ [$\gamma(CO)$ of NaCo(CO)$_4$] with absorption bands simultaneously appearing at 127, 2071, 2056 and 2044 cm$^{-1}$, which may be assigned to the $\gamma(CO)$ of complex (II).

The ethereal solutions of the catalysts according to the present invention display, to the contrary of the ethereal solutions of the catalysts known from the prior art, a good stability which allows them to be stored, at room temperature, for long time periods, The catalysts according to the present invention have found useful application in the processes for preparing the naphthalene esters (IV) by starting from the corresponding naphthalene mono- and disulfonates (III).

These compounds are caused to react with carbon monoxide, in an alcoholic solvent, in the presence of an acidity acceptor compound and of a catalyst of formula (II), according to the following reaction:

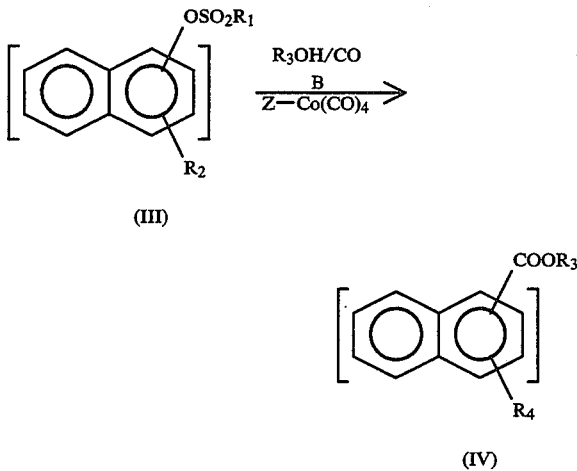

in which
- $R_1$ is a group selected from an alkyl radical of up to 5 carbon atoms; $CF_3$; a 4—$R_5$—phenyl group in which $R_5$ is an H or a halogen atom or a group selected from $NO_2$, $CF_3$, an alkyl of up to 5 carbon atoms, an alkoxy of up to 5 carbon atoms;
- $R_2$ represents a substituent selected from H, an $OSO_2R_1$ moiety in which $R_1$ is as defined hereinabove, a $COOR_6$ moiety, in which $R_6$ is H, or an alkyl radical of up to 5 carbon atoms;
- $R_3$ represents an alkyl radical of up to 5 carbon atoms, preferably selected from methyl, ethyl and isopropyl moieties;
- $R_4$ stands for H or a $COOR_7$ moiety, in which $R_7$ stands for H or an alkyl radical of up to 5 carbon atoms.

When $R_4$=H, the $COOR_3$ moiety indifferently occupies the 1- or 2-positions of the naphthalene ring (IV).

When $R_4$=$COOR_7$, the relative positions occupied by both moieties may be 1,2-; 1,3-; 1,4-; 1,5-; 1,6-; 7-; 1,8-; 2,3-; 2,6-; 2,7-positions; and preferably 1,5-; 2,6-; 2,7-positions (IV).

When $R_4$ is H or COOH and $R_3$=H, the naphthalene carboxy acids are obtained, which can also be produced by means of known techniques, such as by saponifying the corresponding esters in an either acidic or basic medium.

The naphthalene sulfonates are obtained by reacting a naphthol with a sulfonylating agent, as disclosed in Italian patent application MI 92 A 000 485.

The acidity acceptor (B) is an either inorganic or organic base, preferably selected from $K_2CO_3$, $Na_2CO_3$, $Cs_2CO_3$, $R_3$—ONa (i.e., an alkoxide derived from the same alcohol $R_3OH$ used as the solvent), or tertiary amines of formula $NR_8R_9R_{10}$ wherein the substituents, which may be the same or different from each other, can be alkyl or cycloalkyl radicals containing from 1 to 10 carbon atoms.

When an alkoxide is used, it can be separately prepared, or can be produced in situ by causing the alcohol $R_3OH$ to react with an alkali metal.

The useable solvents are the alcohols having formula $R_3OH$ wherein $R_3$ is an alkyl radical containing up to 5 carbon atoms; they are preferably selected from methyl alcohol, ethyl alcohol and isopropyl alcohol.

Suitable solvents for the catalyst are ethers, in particular ethyl ether, hydrocarbons and alcohols.

The molar ratio of the sulfonate to the catalyst can range within wide limits. In general, said ratio is comprised within the range of from 5:1 to 100:1 and, preferably, of from 10:1 to 30:1.

The reaction is complete within a time of from 1 to 12 hours, according to the temperature, the reactants concentration and the catalyst (II) addition rate.

The reaction is carried out under atmospheric pressure and at temperatures comprised within the range of from $-10°$ C. to 60° C., and preferably of from 20° C. to 50° C.

The process can be practically carried out as follows.

To a thermostatted reactor provided with stirrer and reflux condenser, the solvent, the acidity acceptor compound (B) and the sulfonate (III) are added under a CO atmosphere.

After increasing the mixture to the desired temperature, the prefixed amount of catalyst (II), dissolved in a suitable solvent and kept at 25° C., is gradually added with stirring.

During the addition of the catalyst, the reaction progress is displayed by the absorption of CO.

When the reaction is ended, the reaction mixture is diluted with water, is acidified and is extracted with $CH_2Cl_2$. After evaporating $CH_2Cl_2$ off, the ester is isolated by means of well-known techniques (e.g., by distillation or crystallization), or it can be saponified in order to yield the corresponding free acid.

The following examples are reported in order to further illustrate the process according to the present invention and shall not be construed as being limitative of the purview of said invention, which is only as defined by the appended claims.

EXAMPLE 1

To a solution of 0.1 g (0.51 mmol) of $NaCo(CO)_4$ in 10 ml of ethyl ether, kept at 0° C. under an argon atmosphere, 0.095 g (0.51 mmol) of s-trichloro triazine is added. The reaction mixture is kept 2 hours at 0° C. and the temperature is subsequently increased up to 25° C. Sodium chloride, which precipitates off quantitatively during the reaction, is filtered off and then the disappearance of the $NaCo(CO)_4$ absorption band at 1900 cm$^{-1}$, and the appearance of the absorption bands at 2127, 2071, 2056 and 2044 cm$^{-1}$, assignable to complex (II), are checked by I.R. analysis.

The resulting solution is used for the catalytic carbonylation of naphthalene mono- and disulfonates.

EXAMPLE 2

To a solution of 1.0 g (5.1 mmol) of $NaCo(CO)_4$ in 100 ml of ethyl ether, kept at 0° C. under an argon atmosphere, 0.95 g (5.1 mmol) of s-trichloro triazine is added, during approximately one minute. The reaction mixture is kept 2 hours at 0° C. and the temperature is subsequent ly inc reased up to 25° C. Sodium chloride, which precipitates off quantitatively during the reaction, is filtered off, and then the disappearance of the $NaCo(CO)_4$ absorption band at 1900 cm$^{-1}$, and the appearance of the absorption bands at 2127, 2071, 2056 and 2044 cm$^{-1}$, assignable to the complex (II), are checked by I.R. analysis.

Aliquots of the resulting solution, which appears to remain stable during some weeks, can be used for the catalytic carbonylation of naphthalene mono- and disulfonates.

EXAMPLE 3

1.06 g (5.16 mmol) of 2-(4-methylbenzenesulfonyl-naphthalene), 0.82 g (5.9 mmol) of $K_2CO_3$, 20 ml of methanol are charged under a CO pressure, to a reactor of 50 ml, equipped with magnetic stirrer, thermometer and addition funnel. The temperature is increased up to 45° C. and, through the addition funnel, 10 ml (0.5 mmol) is added of a 0.05 M solution of Z-Co(CO)$_4$ catalyst in ethyl ether. The addition is carried out dropwise and with a constant rate, and the reaction mixture is kept stirred until the absorption of carbon monoxide is ended (95 minutes). The reaction products are isolated by treating the resulting reaction mixture with 20 ml of acidic water (0.1M HCl) and extraction with 2×40 ml of $CH_2Cl_2$. By evaporating off the organic solvent under vacuum, 0.72 g (3.87 mmol) of 2-methoxycarbonylnaphthalene and 0.38 g (1.29 mmol) of unreacted 2-(4-methylbenzenesulfonylnaphthalene) are obtained. The composition of the reaction mixture is determined by NMR analysis after the addition of an internal standard.

EXAMPLE 4

The reaction is carried out as in Example 3, by using 1.54 g (5.16 mmol) of 1-(4-methylbenzenesulfonylnaphthalene) as substrate; 0.72 g (3.87 mmol) of 1-methoxycarbonylnaphthalene, 0.07 g (0.48 mmol) of 1-naphthol and 0.21 g (0.72 mmol) of unreacted 1-(4-methylbenzenesulfonylnaphthalene) are obtained.

EXAMPLE 5

The reaction is carried out as in Example 3, by using 1.9 g (5.33 mmol) of 2-(4-methylbenzenesulfonyl)-4-carbomethoxynaphthalene) as substrate; 0.86 g (3.52 mmol) of 2,6-dimethoxycarbonylnaphthalene, 0.10 g (0.53 mmol) of 2-hydroxy-6-carbomethoxynaphthalene and 0.43 g (1.22 mmol) of unreacted 2-(4-methylbenzenesulfonyl)-4-carbomethoxy-naphthalene) are obtained.

EXAMPLE 6

The reaction is carried out as in Example 3, by using 1.0 g (2.15 mmol) of 2,6-bis-(4-methyl-benzenesulfonyl)-naphthalene as substrate; 0.37 g (1.5 mmol) of 2,6-dimethoxycarbonyl-naphthalene is obtained.

EXAMPLE 7

The reaction is carried out as in Example 3, by using 1.0 g (2.15 mmol) of 2,7-bis-(4-methyl-benzenesulfonyl)-naphthalene as substrate; 0.15 g (0.61 mmol) of 2,7-dimethoxycarbonyl-naphthalene is obtained.

EXAMPLE 8

The reaction is carried out as in Example 3, by using 1.6 g (5.3 mmol) of 1-(4-fluoro-benzenesulfonyl)-naphthalene as substrate; 0.67 g (3.6 mmol) of 1-methoxycarbonyl-naphthalene is obtained.

We claim:

1. Catalyst for naphthalene mono- and disulfonates carbonylation having the formula (II):

$$Z-Co(CO)_4 \quad (II)$$

in which Z stands for the 2,5-dichloro-1,3,5-triazinyl radical:

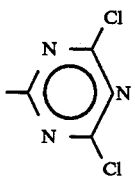

2. Method for preparing the catalyst according to claim 1, which consists in causing the sodium salt of cobalt tetracarbonyl NaCo(CO)$_4$ to react with s-trichloro triazine, in an organic solvent, at temperatures comprised within the range of from −10° C. to 25° C., and subsequently submitting the solution to filtration.

3. Method for preparing the catalyst according to claim 2, in which the reaction is carried out in ether.

4. Method for preparing the catalyst according to claim 2 in which the reaction temperature is kept at 0° C.

5. Process for preparing naphthalene esters and acids, consisting in carbonylating naphthalene nono- and disulfonates with carbon monoxide, in an alcoholic solvent, at atmospheric pressure, at temperatures comprised within the range of from −20° C. to 60° C., in the presence of an acidity acceptor compound and of a catalyst which, in its active form, is constituted by a cobalt complex of formula (II).

6. Process for preparing naphthalene esters and acids according to claim 5 in which the starting products are naphthalene sulfonates of formula (III):

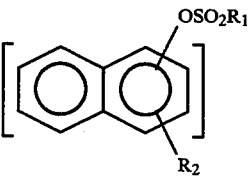

in which

R$_1$ is a group selected from an alkyl radical of up to 5 carbon atoms; CF$_3$; a 4-R$_5$-phenyl group in which R$_5$ is an H or a halogen atom or a group selected from NO$_2$, CF$_3$, an alkyl of up to 5 carbon atoms, an alkoxy of up to 5 carbon atoms, R$_2$ represents a substituent selected from H, an OSO$_2$R$_1$ moiety in which R$_1$ is as defined hereinabove, a COOR$_6$ moiety, in which R$_6$ is H, or an alkyl radical of up to 5 carbon atoms.

7. Process for preparing naphthalene esters and acids according to claim 5, in which the obtained products are compounds of formula (IV)

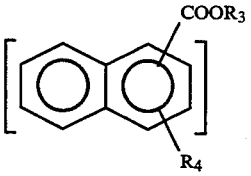

in which $R_3$ represents an alkyl radical of up to 5 carbon atoms, preferably selected from methyl, ethyl and isopropyl moieties;

$R_4$ stands for H or a $COOR_7$ moiety, in which $R_7$ stands for H or an alkyl radical of up to 5 carbon atoms;

when $R_4$=H, the $COOR_3$ moiety indifferently occupies the 1- or 2-positions of the naphthalene ring; when $R_4$=$COOR_7$, the relative positions occupied by both moieties may be the 1,2-; 1,3-; 1,4-; 1,5-; 1,6-; 1,7-; 1,8-; 2,3-; 2,6-; 2,7-positions.

8. Process for preparing naphthalene esters and acids according to claim 5, in which the molar ratio of the sulfonate to the catalyst is comprised within the range of from 5:1 to 100:1.

9. Process for preparing naphthalene esters and acids according to claim 8, in which the molar ratio of sulfonate to catalyst is comprised within the range of from 10:1 to 30:1.

10. Process for preparing naphthalene esters and acids according to claim 5, in which the acidity acceptor (B) is an inorganic base, selected from $K_2CO_3$, $Na_2CO_3$, $Cs_2CO_3$, $R_3$-ONa (i.e., an alkoxide derived from the same alcohol $R_3OH$ used as the solvent).

11. Process for preparing naphthalene esters and acids according to claim 5, in which the acidity acceptor (B) is an organic base, selected from tertiary amines of formula $NR_8R_9R_{10}$ wherein the substituents, which may be the same or different from each other, can be alkyl or cycloalkyl radicals containing from 1 to 10 carbon atoms.

12. Process for preparing naphthalene esters and acids according to claim 5, in which the solvent used is selected from the alcohols having formula $R_3OH$ wherein $R_3$ is an alkyl radical containing up to 5 carbon atoms.

13. Process for preparing naphthalene esters and acids according to claim 12, in which the solvent used is selected from methyl, ethyl and isopropyl alcohols.

14. Process for preparing naphthalenic esters and acids according to claim 5, in which the reaction is carried out at a temperature comprised within the range of from 20° C. to 50° C.

* * * * *